(12) United States Patent
Zhang et al.

(10) Patent No.: US 8,050,730 B2
(45) Date of Patent: Nov. 1, 2011

(54) METHOD AND APPARATUS FOR ELIMINATING INTERFERENCE IN PULSE OXYGEN MEASUREMENT

(75) Inventors: Xu Zhang, Shenzhen (CN); Xu Li, Shenzhen (CN); Shunan Li, Shenzhen (CN)

(73) Assignee: Shenzhen Mindray Bio-Medical Electrics Co., Ltd. (CN)

(*) Notice: Subject to any disclaimer, the term of this patent is extended or adjusted under 35 U.S.C. 154(b) by 1444 days.

(21) Appl. No.: 11/522,396

(22) Filed: Sep. 18, 2006

(65) Prior Publication Data
US 2007/0149872 A1    Jun. 28, 2007

(30) Foreign Application Priority Data

Dec. 23, 2005   (CN) .......................... 2005 1 0121269
Jul. 7, 2006    (CN) .......................... 2006 1 0061601

(51) Int. Cl.
*A61B 5/1455* (2006.01)
(52) U.S. Cl. ........................ 600/336; 600/323
(58) Field of Classification Search ................ 600/310, 600/322, 323, 336
See application file for complete search history.

(56) References Cited

U.S. PATENT DOCUMENTS

| | | | |
|---|---|---|---|
| 3,811,040 A | 5/1974 | Weinfurt et al. | |
| 4,648,120 A * | 3/1987 | Chittineni | 382/266 |
| 4,807,631 A | 2/1989 | Hersh et al. | |
| 5,485,847 A | 1/1996 | Baker, Jr. | |
| 5,588,427 A * | 12/1996 | Tien | 600/323 |
| 5,687,722 A * | 11/1997 | Tien et al. | 600/323 |
| 5,758,644 A | 6/1998 | Diab et al. | |
| 5,788,927 A | 8/1998 | Farrell et al. | |
| 5,853,364 A | 12/1998 | Baker, Jr. et al. | |
| 5,995,858 A * | 11/1999 | Kinast | 600/323 |
| 6,083,157 A * | 7/2000 | Noller | 600/310 |
| 6,094,592 A | 7/2000 | Yorkey et al. | |
| 6,122,535 A * | 9/2000 | Kaestle et al. | 600/322 |

(Continued)

FOREIGN PATENT DOCUMENTS

AU     199670364 A1   10/1996

(Continued)

OTHER PUBLICATIONS

Notice of Allowance mailed Nov. 7, 2008, for U.S. Appl. No. 11/316,060, filed Dec. 22, 2005.

(Continued)

*Primary Examiner* — Eric Winakur
*Assistant Examiner* — Chu Chuan (JJ) Liu
(74) *Attorney, Agent, or Firm* — Vista IP Law Group, LLP

(57) ABSTRACT

The present invention discloses a method and apparatus for eliminating interference in pulse oxygen measurement. The method comprises the steps of: collecting a first wavelength light and a second wavelength light transmitting through the object to be measured and converting collected optic signals into electric signals to form a plethysmogram; processing the plethysmogram so as to normalize it, in order to decompose the normalized plethysmogram into a combination of an ideal plethysmogram and noise, and expand the ideal plethysmogram by using functions that can make up a complete orthonormal system; eliminating the noise in the plethysmogram through differential operation; and restoring the plethysmogram free of noise through integral operation for calculating oxygen saturation. The apparatus comprises a collecting module, a processing module, a noise eliminating module, and a restoring module. The method and apparatus suitable for the measurement of oxygen saturation under weak perfusion and movement conditions.

20 Claims, 12 Drawing Sheets

U.S. PATENT DOCUMENTS

| | | |
|---|---|---|
| 6,151,107 A | 11/2000 | Schollermann et al. |
| 6,157,850 A | 12/2000 | Diab et al. |
| 6,334,065 B1 | 12/2001 | Al-Ali et al. |
| 6,713,019 B2 | 3/2004 | Ozasa et al. |
| 2003/0036689 A1 | 2/2003 | Diab et al. |
| 2004/0044276 A1 | 3/2004 | Arnold |

FOREIGN PATENT DOCUMENTS

| | | |
|---|---|---|
| CN | 1104475 A | 7/1995 |
| CN | 1148794 A | 4/1997 |
| CN | 1358075 A | 7/2002 |
| CN | 1365649 A | 8/2002 |
| CN | 1600271 A | 3/2005 |
| JP | 2003153882 A | 5/2003 |
| JP | 2004202190 A | 7/2004 |
| WO | 98/17174 A1 | 4/1998 |

OTHER PUBLICATIONS

Office Action mailed Jun. 17, 2008, for U.S. Appl. No. 11/316,060, filed Dec. 22, 2005.

* cited by examiner

METHOD AND APPARATUS FOR ELIMINATING INTERFERENCE IN PULSE OXYGEN MEASUREMENT

STATEMENT OF RELATED APPLICATION

The present application claims the priority of the Chinese Patent Application No. 200510121269.6, filed on Dec. 23, 2005, entitled "Apparatus and Method for Pulse Oxygen Saturation Measurement Capable of Eliminating the Interference of Motion" and the Chinese Patent Application No. 200610061601.9, filed on Jul. 7, 2006, entitled "Method for AC Component Measurement and the Apparatus thereof", the disclosure of which is incorporated herein by reference.

FIELD OF THE INVENTION

The present invention relates to a method and apparatus for measuring oxygen saturation for medical use, and more particularly to a method and apparatus for eliminating interference in oxygen saturation measurement.

BACKGROUND OF THE INVENTION

As currently employed in home and abroad, a oxygen saturation measuring apparatus (also known as oximeter) usually measures the oxygen saturation via spectrophotometry which comprises a transmission method and reflection method. Both methods are based on the Lambert-Beer law and light-scattering theory, and are carried out by making use of the difference of the photoabsorption coefficients between a deoxyhemoglobin and an oxyhemoglobin. The Lambert-Beer law is formulated as:

$$I = I_0 e^{-\epsilon cd}$$

where:
I represents transmitted light intensity;
$I_0$ represents incident light intensity;
C represents concentration of solution of the photic substance;
d represents photic path length of the solution;
$\epsilon$ represents photoabsorption coefficient of the substance;
from the above equation, it is derived that:

$$D = \ln I_0/I = \epsilon cd;$$

where D is known as optical density. The formula reveals that there exists a correlation between the photoabsorption state of a substance and its concentration. In other words, the formula gives the very indication of the possibility of predicating internal tissue components from the photoabsorption state of the tissue.

Researchers further study the photoabsorption property of two main components, i.e., Hb (deoxyhemoglobin) and $HbO_2$ (oxyhemoglobin), which are closely related to the oxygen saturation, and find remarkable difference therebetween. As shown in FIG. 2, the solid line represents the $HbO_2$ photoabsorption coefficient curve, and the dotted line represents the Hb photoabsorption coefficient curve. It can be seen from FIG. 2 that at the visible red light range with wavelength of 660 nm, the photoabsorption coefficient of $HbO_2$ is only 1/10 that of Hb; at the 805 nm infrared light range, Hb and $HbO_2$ has a isosbestic point; and at the 940 nm infrared light range, the photoabsorption coefficient of $HbO_2$ is greater than that of Hb.

$$SaO_2 = HbO_2/(Hb + HbO_2) = c_1/(c_1 + c_2), \quad (1)$$

$$\begin{aligned} D(660) &= \ln I_0(660)/I(660) \\ &= \ln(I_0(660)/I(660)e^{-\epsilon_1 c_1 d}e^{-\epsilon_2 c_2 d}) \\ &= \epsilon_1 c_1 d + \epsilon_2 c_2 d, \end{aligned} \quad (2)$$

$$\begin{aligned} D(805) &= \ln I_0(805)/I(805) \\ &= \ln(I_0(805)/I(805)e^{-\epsilon_3 c_1 d}e^{-\epsilon_4 c_2 d}) \\ &= \epsilon_3 c_1 d + \epsilon_4 c_2 d, \end{aligned} \quad (3)$$

where $SaO_2$ is the arterial oxygen saturation; $c_1$ is $HbO_2$ concentration, and $c_2$ is Hb concentration; $I_0$, I are incident light intensity and transmitted light intensity respectively; $\epsilon_1$, $\epsilon_2$ are the absorptivity of $HbO_2$ and Hb to the red light of 660 nm wavelength respectively; $\epsilon_3$, $\epsilon_4$ are the absorptivity of $HbO_2$ and Hb to the infrared light of 805 nm wavelength respectively, with $\epsilon_3 = \epsilon_4 = \epsilon$; and d is the tissue transmission thickness. From (2) and (3) it is derived that:

$$c_1 + c_2 = D(805)/\epsilon d,$$

$$c_1 = (D(660) - \epsilon_2 D(805)/\epsilon)/(\epsilon_1 - \epsilon_2)d;$$

substituting them into (1):

$$SaO_2 = A \times D(660)/D(805) + B \quad (4)$$

where, $A = \epsilon/(\epsilon_1 - \epsilon_2)$, $B = \epsilon_2/(\epsilon_1 - \epsilon_2)$.

However, D(660) and D(805) are not correlated with Hb and $HbO_2$ only, as expressed in the above equations (2) and (3). Rather, they are correlated with the absorption conditions of the muscle, skeleton, pigment, fats, venous blood and the like in the tissue. In other words, D(660), D(805) should contain a background absorption portion, as shown in FIG. 3. Thus (2) and (3) transform into:

$$D(660) = \ln I_0(660)/I(660) = \ln(I_0(660)/I_B e^{-\epsilon_1 c_1 \Delta d} e^{-\epsilon_2 c_2 \Delta d}), \quad (5)$$

$$D(805) = \ln I_0(805)/I(805) = \ln(I_0(805)/I_B e^{-\epsilon_3 c_1 \Delta d} e^{-\epsilon_4 c_2 \Delta d}), \quad (6)$$

where $I_0$ is the transmitted light intensity when only the tissue background absorption exits; $\Delta d$ is the variation in the transmission range from absence of blood to abundance of blood. The background optic density $D_B$ may be simply defined as:

$$D_B = \ln(I_0/I_B),$$

thus:

$$D(660) - D_B(660) = \epsilon_1 c_1 \Delta d + \epsilon_2 c_2 \Delta d, \quad (7)$$

$$D(805) - D_B(805) = \epsilon_3 c_1 \Delta d + \epsilon_4 c_2 \Delta d, \quad (8)$$

where $\epsilon_3 = \epsilon_4 = \epsilon$, and (4) accordingly transforms into:

$$SaO_2 = A \times (D(660) - D_B(660))/(D(805) - D_B(805)) + B; \quad (9)$$

A and B are the same as above. Formula (9) is the basic formula for oxygen saturation measurement.

In a typical measurement, the infrared light wavelength usually adopted is about 940 nm, around which both the absorptivity of $HbO_2$ and that of Hb vary flat, and the error is often relatively small. The basic calculation formula for oxygen saturation measurement is:

$$Spo_2 = (A \times R + B)/(C \times R + D); \quad (10)$$

where:
$SpO_2$ is the oxygen saturation, $$A = \varepsilon_1,$$
$$B = -\varepsilon_2,$$
$$C = \varepsilon_4 - \varepsilon_3,$$
$$D = \varepsilon_1 - \varepsilon_2,$$
$$\text{while } R = \frac{D(660) - D_B(660)}{D(940) - D_B(940)}.$$
(11)

$\varepsilon_1$, $\varepsilon_2$ are the absorptivity of $HbO_2$ and Hb to red light of 660 nm wavelength, respectively; $\varepsilon_3$, $\varepsilon_4$ are the absorptivity of $HbO_2$ and Hb to infrared light of 940 nm wavelength, respectively.

From (11), it can be seen that R is in one-to-one correspondence with oxygen saturation, while $D = \ln I_0/I = \varepsilon cd$, $$\text{thus } R = \frac{\ln I_{R0}/I_{RM} - \ln I_{R0}/I_{Rm}}{\ln I_{I0}/I_{IM} - \ln I_{I0}/I_{Im}} = \frac{\ln I_{Rm}/I_{RM}}{\ln I_{Im}/I_{IM}};$$
(12)

where, $I_{RM}$ is the maximum transmitted light intensity of the red light; $I_{Rm}$ is the minimum transmitted light intensity of the red the optic signals with oxygen saturation information passing through the tissue terminals into an electric signals, and to digitalize the signals. With this numerical value, the oxygen saturation is then calculable by certain signal processing algorithm. FIG. 1 illustrates the block diagram of the structure of one particular embodiment in prior art, comprising: a power supply circuit, a photoelectric drive circuit, a signal amplification section, an A/D conversion circuit, a logic control section, a single chip processor, and a serial communication interface.

A pulse oximeter makes use of arterial blood pulsation in the human body tissue terminals, which is caused by the plethysmogram. The optical properties of the oxyhemoglobin and deoxyhemoglobin in the red light spectral region and the infrared region are different, which influences the red light and infrared light transmission of the finger. Hence, when the red light and the infrared light with a predetermined intensity are applied to the finger, by respectively detecting the transmitted light intensity of the two wavelengths, the oxyhemoglobin content can be calculated by the ratio between the optical density variations in the two light beams applied to the finger, so that the oxygen saturation may be calculated.

It can be derived from the above formula that when the luminotron is fixed, the formula (10) only has one variable R. The DC components of the red light and the infrared light (i.e., the DC components of the electric signals produced from the red light and light; $I_{R0}$ is the incident light intensity of the red light; $I_{IM}$ is the maximum transmitted light intensity of the infrared light; $I_{Im}$ is the minimum transmitted light intensity of the infrared light; $I_{I0}$ is the incident light intensity of the infrared light.

As for the red light, $$\ln I_{Rm}/I_{RM} = \ln\left(1 - \frac{I_{RM} - I_{Rm}}{I_{RM}}\right);$$
(13)

when the AC quantity/DC quantity, i.e. $(I_{RM} - I_{Rm})/I_{RM}$, is relatively small, $$\ln\left(1 - \frac{I_{RM} - I_{Rm}}{I_{RM}}\right) \approx \frac{I_{RM} - I_{Rm}}{I_{RM}} \approx \text{AC quantity/DC quantity,}$$

thus R may be expressed in the following form:

$$R = \frac{Red_{AC}/Red_{DC}}{Ir_{AC}/Ir_{DC}} = \frac{Red_{AC}}{Red_{DC}} \cdot \frac{Ir_{DC}}{Ir_{AC}} = \frac{Ir_{DC}}{Red_{DC}} \cdot \frac{Red_{AC}}{Ir_{AC}}.$$

Therefore, the value of R can be calculated in case the waveform of one full plethysmogram of the two transmitted light beams is available.

The basic structure of the oxygen saturation measurement apparatus comprises a probe and a signal processing means, in which the probe is a sensor composed of a light-emitting diode and a light sensitive element. The light-emitting diode generates light with two or more wavelengths, usually the red light and the infrared light. The light sensitive element functions to convert the infrared light, similar hereinafter) remain relatively stable within a certain period, so the main factor influencing the value of R is the AC components of the red light and the infrared light (i.e., the AC components of the electric signals produced from the red light and the infrared light, similar hereinafter). Therefore the oxygen saturation can be calculated so long as the AC components of two light beams are available. The conventional method of calculating the ratio between the AC components is to determine the maximum value and the minimum value of the two light beams. However, such a method of calculating the AC components of the two light beams by determination of extreme values has the following drawbacks.

1) When the patient to be measured is in a state of anaesthesia, the plethysmogram of the patient may be very weak. In such a weak perfusion condition, even if there is no change in the luminescent intensity of the probe, irregular baseline drift often occurs to the received signal. Though such a drift is nonlinear, it can be approximated by the multi-order linear functions, and the approximation error is neglectable when the measurement precision is satisfied. Such a drift generates a very strong low frequency interference in the signal spectrum, while it generates a very strong interference with the pulse oxygen and pulse calculation when it is within the measuring frequency band so as to heavily influence the pulse oxygen calculation and lead to a great error.

2) When the patient is in a state of weak perfusion, the signal is very weak. Thus the signal-to-noise ratio is very low, the determination of the waveform at this point is very difficult. Since the determination of the crest and trough of the plethysmogram may result in error, the ratio of the AC component to DC component would be incorrect, and accordingly it is hard to ensure the accuracy of the pulse oxygen and pulse rate measurement.

3) While monitoring the pulse oxygen of a patient, the probe of the oximeter is usually bonded to the foot of the patient. However, the patient will move unconsciously, which is the case in particular with infants and the new-born babies. For instance, the fingers (or toes) of the patient often move, so that the distance between the fingers (or toes) and the sensor is changed, resulting in a very unstable plethysmogram waveform measured and a rather low signal-to-noise ratio. If the pulse oxygen is to be measured with a prior art method, it is necessary to measure the AC component of the plethysmogram. That is, the maximum value and the minimum value of the plethysmogram waveform should be located. However, in case of the presence of movement, the crest and trough of the plethysmogram waveform may be incorrectly determined and it is very difficult to obtain the accurate extreme values, so that the pulse oxygen measuring precision is very poor. As shown in FIG. 4, a moving condition will bring about, for example, baseline drift, impulsive noise, step noise and the like, to the plethysmogram, and at this moment it is very difficult to correctly determine the extreme values of the two light beams.

SUMMARY OF THE INVENTION

The main object of the present invention is to resolve the above problem by providing a method and apparatus for eliminating interference in pulse oxygen measurement, to eliminate the nonlinear baseline drift in the waveforms of the two transmitted light beams, and improve the accuracy of the AC component measurement; minimize the influence of the random noise and further improve the accuracy of the AC component measurement; and maintain the effect of the previous measurement as well as allow a real time measurement. This object is achieved by the following solutions.

According to the first aspect of the present invention, there is provided a method for eliminating interference in pulse oxygen measurement, comprising the following steps of: collecting a first wavelength light and a second wavelength light transmitting through an object to be measured and converting collected optic signals into electric signals so as to form a plethysmogram; processing the plethysmogram so as to normalize it, in order to decompose normalized plethysmogram into a combination of an ideal plethysmogram and a noise, and expand the ideal plethysmogram by using functions that can make up a complete orthonormal system; eliminating the noise in the plethysmogram through differential operation; and restoring the plethysmogram free of the noise through integral operation for calculating oxygen saturation.

The method for eliminating interference in pulse oxygen measurement according to the present invention optionally comprises the step of conducting an analog-to-digital conversion to the electric signals so as to form a digitalized plethysmogram for the subsequent processing.

The method for eliminating interference in pulse oxygen measurement according to the present invention optionally further comprises a fitting step, for calculation of oxygen saturation after elimination of the nonlinear slow baseline drift, which further comprises: computing the respective drift baseline fitting curve coefficient matrixes according to sampling frequencies and sampling sequences of the transmitted light intensity of the first wavelength light and the second wavelength light; and subtracting the corresponding fitting curves from the plethysmogram waveform curves of the transmitted first wavelength light and second wavelength light.

Preferably, in the processing step, the ideal plethysmogram may be expanded by sine functions and cosine functions that make up a complete orthonormal system. The noise eliminating step is realized by: differentiating the plethysmogram having been processed, and then normalizing it to eliminate the baseline drift noise caused by movement. The noise eliminating step may also be realized by: differentiating the plethysmogram having been processed to transform the step noise caused by abrupt extrusion of the object to be measured into an impulse function similar to the $\delta$ function, and subsequently conducting a three-point or five-point median filtering to eliminate the step noise. The noise eliminating step may additionally be realized by: differentiating the plethysmogram having been processed to transform the impulsive noise caused by mutation of the sampled value into positive and negative double impulse functions, and subsequently conducting a five-point median filtering to eliminate the impulse noise.

Preferably, the oxygen saturation calculation is carried out by an area integration recursive algorithm, comprising: integrating the plethysmogram having been restored in a period of time to eliminate the white noise occurring in the same time period and obtain the ratio between the AC component of the first wavelength light and that of the second wavelength light; introducing a forgetting factor $\lambda$, to obtain the ratio between the AC component of the first wavelength light and that of the second wavelength light according to the following formula after iterating for a number of times:

$$\frac{Red_{AC}}{Ir_{AC}} = \frac{Red_{AC_0} + \lambda Red_{AC_1} + \ldots + \lambda^n Red_{AC_n}}{Ir_{AC_0} + \lambda Ir_{AC_1} + \ldots + \lambda^n Ir_{AC_n}}.$$

Preferably, the time period for the integration ranges from 2 to 3 seconds, and the forgetting factor satisfies: $0<\lambda<1$, preferably 0.8. The first wavelength light and the second wavelength light are the red light and the infrared light respectively.

According to the second aspect of the present invention, there is provided an apparatus for eliminating interference in pulse oxygen measurement, comprising: a collecting module including a luminotron and a corresponding phototube, for collection of a first wavelength light and a second wavelength light transmitting through an object to be measured and for converting collected optic signals into electric signals so as to form a plethysmogram; a processing module, for normalization of the plethysmogram so as to decompose the normalized plethysmogram into a combination of an ideal plethysmogram and a noise, and for expansion of the ideal plethysmogram by using functions that can make up a complete orthonormal system; a noise eliminating module, for elimination of the noise in the plethysmogram through differential operation; and a restoring module, for restoration of the plethysmogram free of noise through integral operation for calculating oxygen saturation.

The apparatus for eliminating interference in pulse oxygen measurement according to the present invention optionally comprises a converting module, for analog-to-digital conversion of the electric signals so as to form a digitalized plethysmogram for the subsequent processing.

The apparatus for eliminating interference in pulse oxygen measurement according to the present invention optionally further comprises a fitting module, for computing the respective drift baseline fitting curve coefficient matrixes according to sampling frequencies and sampling sequences of the transmitted light intensity of the first wavelength light and the second wavelength light, and subtracting the corresponding fitting curves from the plethysmogram waveform curves of the transmitted first wavelength light and second wavelength light so as to eliminate the nonlinear slow baseline drift.

The fitting module, processing module, noise eliminating module and restoring module may be either a physical module, or a computer-executable software module.

Preferably, the functions that make up a complete orthonormal system are sine functions or cosine functions. The noise eliminating module executes the following functions of: differentiating the plethysmogram having been processed by the processing module, and then normalizing it to eliminate the baseline drift noise caused by movement. The noise eliminating module may also executes the following functions of: differentiating the plethysmogram having been processed by the processing module to transform the step noise caused by abrupt extrusion of the object to be measured into an impluse function similar to the δ function, and subsequently conducting a three-point or five-point median filtering to eliminate the step noise. The noise eliminating module may additionally executes the following functions of: differentiating the plethysmogram having been processed by the processing module to transform the impulsive noise caused by mutation of the sampled value into positive and negative double impulse functions, and subsequently conducting a five-point median filtering to eliminate the impluse noise. The first wavelength light and the second wavelength light are the red light and the infrared light respectively.

The advantageous effects of the present invention are: 1) By differentiation and integration processing of the waveform of the transmitted light intensity, the waveform becomes smoothed, which corresponds to a whitening treatment of the waveform that eliminates the non-white noise from the noise; by area integration of the waveform after differentiation within a sufficiently long time interval, the integral of the noise tends to be zero, thus eliminating the interference of the white noise and obtaining better measurement in both weak perfusion and movement conditions. 2) By fitting processing of the waveform of the transmitted light intensity in weak perfusion condition, nonlinear baseline drift is eliminated and the accuracy of the measurement is improved. 3) Location of the accurate extreme values for each plethysmogram waveform is not necessary, instead, it is only needed to integrate the plethysmogram waveform in a certain time interval. Since the integral of the noise in a time interval tends to be zero, the integrating of the plethysmogram may exclude the influence of the noise. Moreover, It is provable that the integrating result of the plethysmogram is equivalent to the AC component of the plethysmogram. Consequently, the integral result may be used to calculate the oxygen saturation, and the result of the calculation substantially is free of the influence of the movement of the object to be measured.

BRIEF DESCRIPTION OF THE DRAWINGS

The features and advantages of the present invention will become clearer through the detailed description of the embodiments of the present invention in combination with the accompanying figures.

DETAILED DESCRIPTION OF THE INVENTION

Two light beams (usually the red light and the infrared light, which are taken as an example for illustrating the present embodiment) are emitted to transmit through the terminals of a biologic tissue (e.g., foot or hand) or other portions, and the transmitted light of the two light beams are received and subjected to photoelectric conversion and analog-to-digital conversion (or may not subjected to the analog-to-digital conversion, but directly processed as analog signals). The measured data of the two light beams having been normalized, the DC ratio $$\frac{Ir_{DC}}{Red_{DC}}$$

of the two light beams can be obtained thereafter. The normalized plethysmogram waveform may be considered as a combination of a waveform in an ideal case and a noise, while the plethysmogram waveform in an ideal case, regardless of the red light waveform or the infrared light waveform, may be regarded as the synthesis of sine waves in different frequency bands:

$$Red=a_0 \cos(\omega t)+a_1 \cos(2\omega t)+\ldots+a_{n-1} \cos(\omega t)+ n_{Red}=Red_{sig}+n_{Red}, \quad (14)$$

$$Ir=b_0 \cos(\omega t)+b_1 \cos(2\omega t)+\ldots+b_{n-1} \cos(n\omega t)+ n_{Ir}=Ir_{sig}+n_{Ir} \quad (15)$$

where $a_0, a_1, \ldots a_{n-1}$ are the n-th components of the red light spectrum; $Red_{sig}$ is the portion of the red light containing no noise but AC and DC components; $n_{Red}$ is the noise component of the red light and contains white noise and non-white noise; $b_0, b_1, \ldots b_{n-1}$ are the n-th components of the infrared light spectrum; $Ir_{sig}$ is the portion of the infrared light containing no noise but AC and DC components; $n_{Ir}$ is the noise component of the infrared light and contains white noise and non-white noise.

Figure 1:
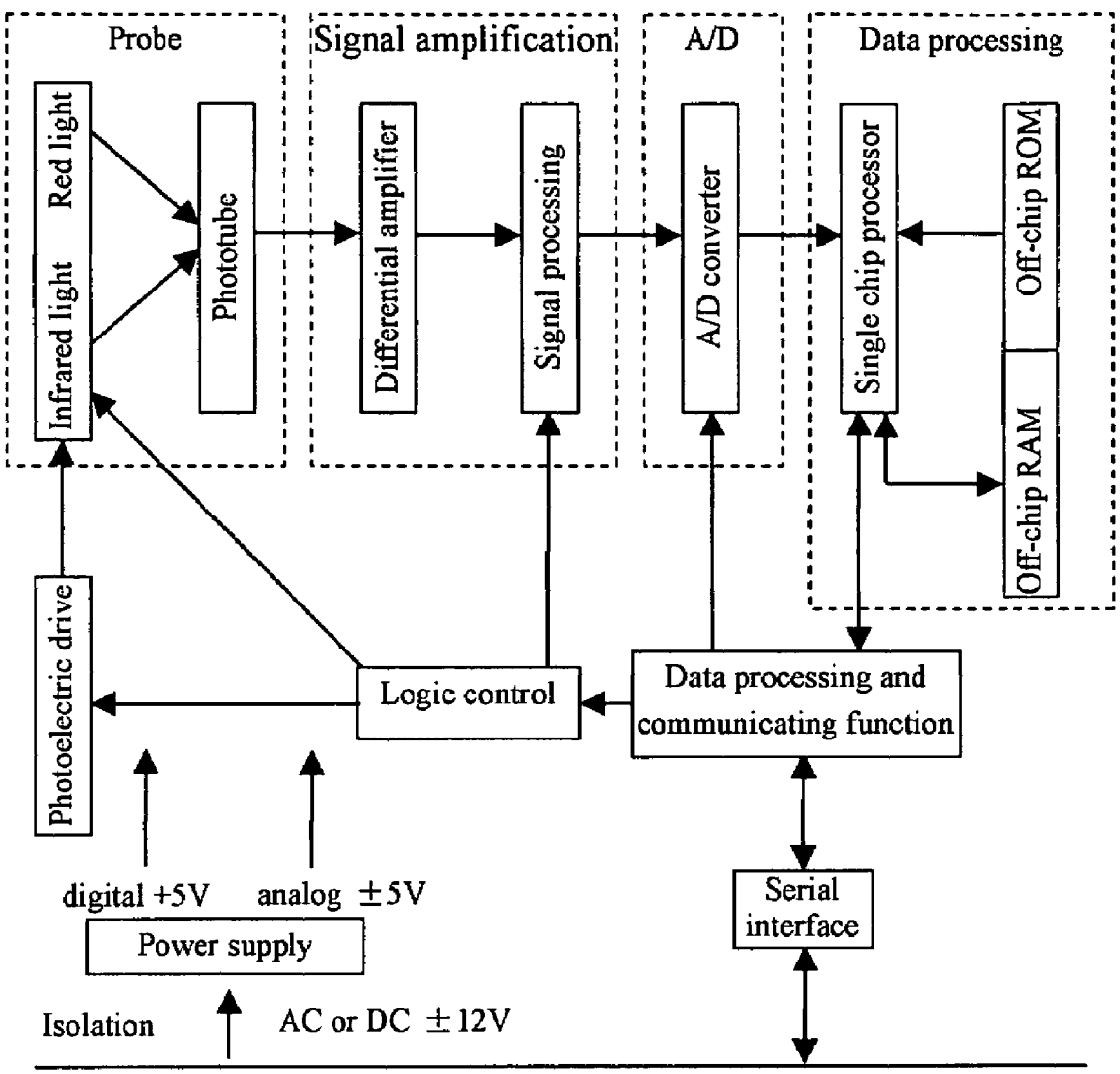
FIG. 1 is the block diagram illustrating the circuit for measuring oxygen saturation in prior art.
Figure 2:
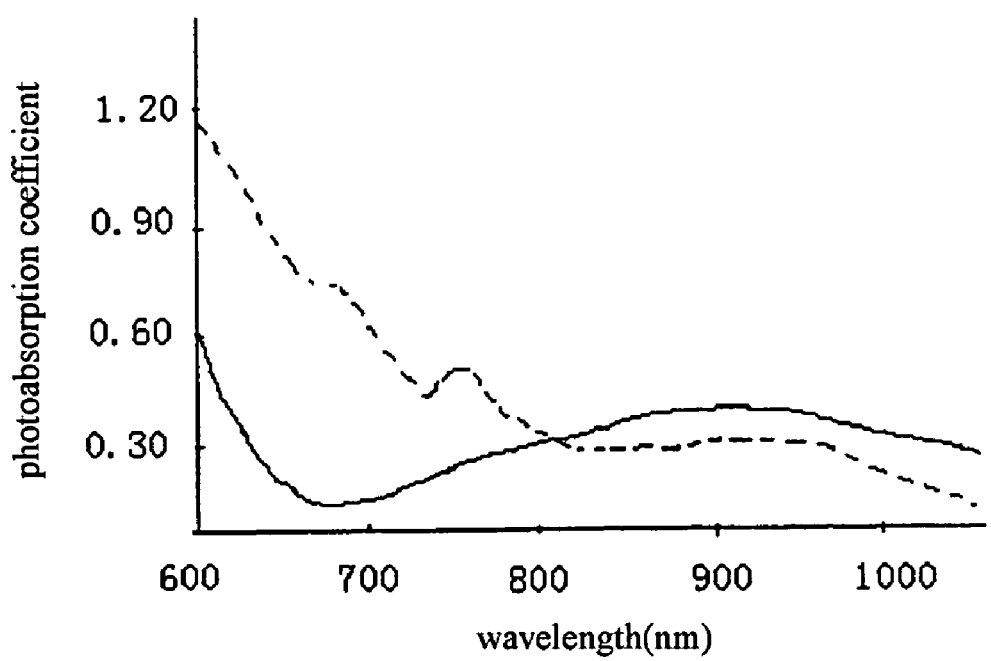
FIG. 2 shows the photoabsorption coefficients of deoxyhemoglobin and oxyhemoglobin at the red light range and the infrared light range.
Figure 3:
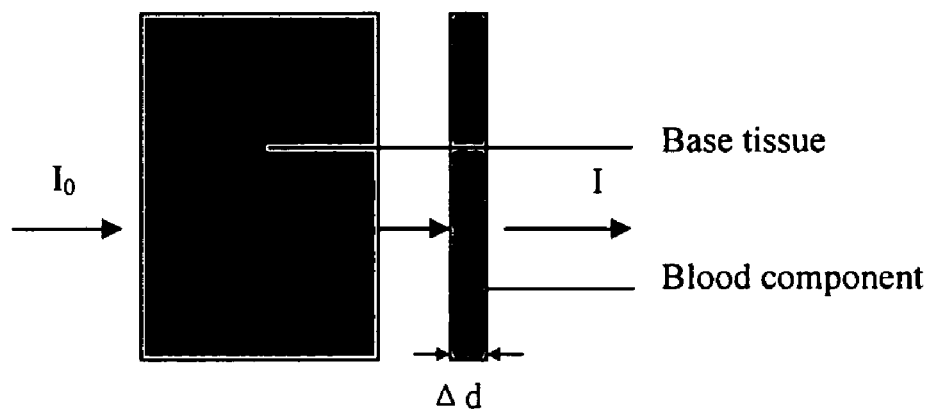
FIG. 3 is an illustration of tissue photoabsorption.
Figure 4:
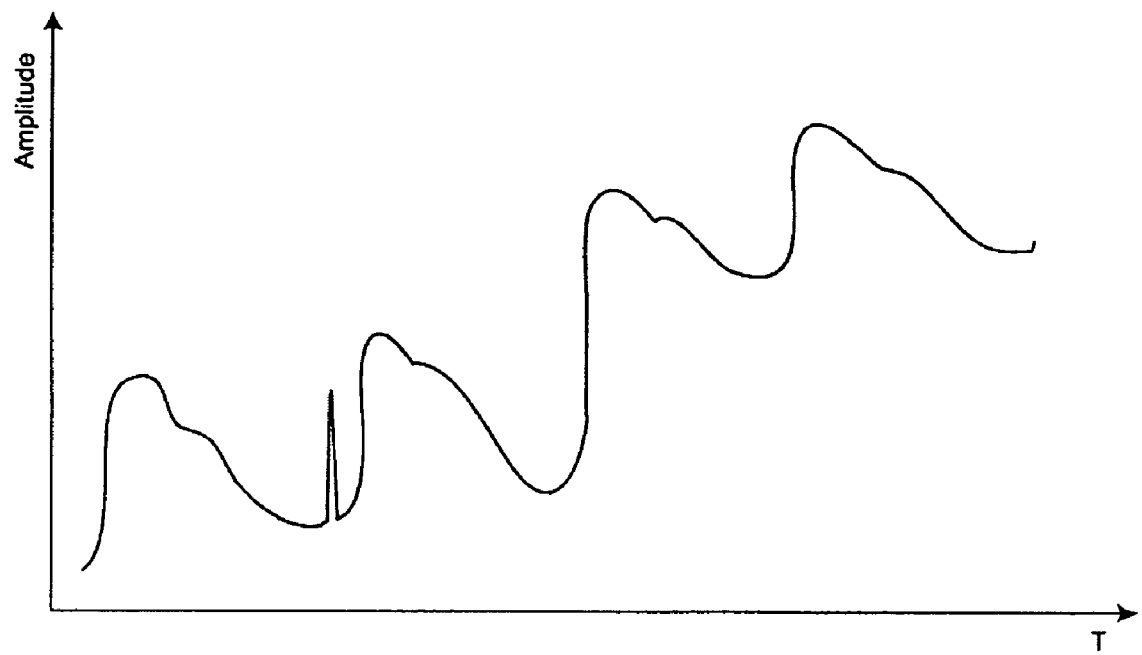
FIG. 4 shows a plethysmogram waveform including noise.

The noise component may be generated by a plurality of circumstances, which may comprise the baseline drift noise due to movement, the noise similar to step change due to abrupt vibration, and the high frequency noise, the waveform of which is shown in FIG. 4.

Hereunder, the elimination of these noises through differentiation, integration, fitting and area integration are explained respectively.

1. Elimination of Linear Baseline Drift by Differentiation

By differentiating the equation (14), (15) respectively, it can by derived that:

$$\frac{dRed}{dt} = \frac{dRed_{sig}}{dt} + \frac{dn_{Red}}{dt}, \quad (16)$$

$$\frac{dIr}{dt} = \frac{dIr_{sig}}{dt} + \frac{dn_{Ir}}{dt}. \quad (17)$$

Figure 5:
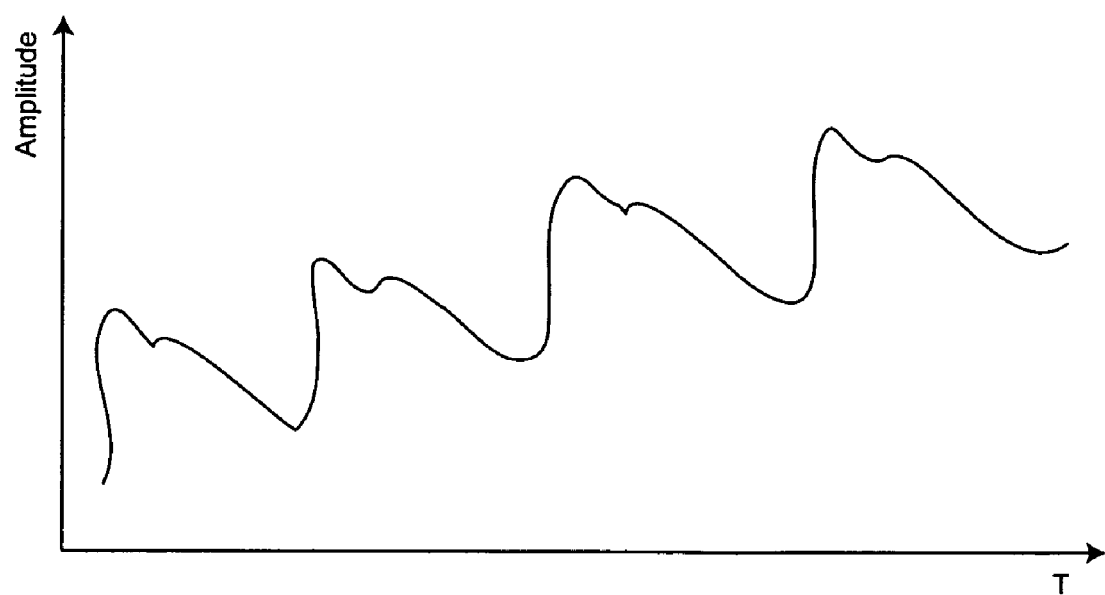
FIG. 5 shows a plethysmogram waveform including baseline drift.
Figure 6:
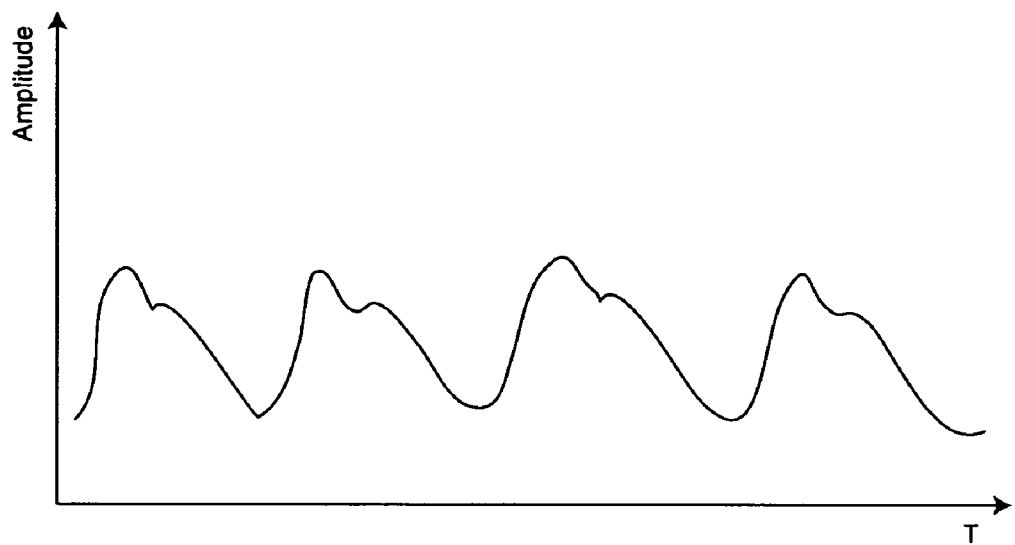
FIG. 6 shows a plethysmogram waveform free of baseline drift.

The DC component of the red light or the infrared light becomes zero after differentiation. As to the plethysmogram including baseline drift as shown in FIG. 5, since the calculation of the pulse oxygen is performed using the sampled data within a time interval and the linear baseline drift within this period becomes constant after differentiation, the noises may be expressed by:

$$\frac{dn_{Red}}{dt} = constn_{red} + n'_{Red}, \quad (18)$$

$$\frac{dI_{Red}}{dt} = constn_{Ir} + n'_{Ir}; \quad (19)$$

where, $constn_{red}$ denotes the constant portion of the red light after differentiation; while $constn_{Ir}$ denotes the constant portion of the infrared light after differentiation. Therefore, the constant portion of the noise having been differentiated can be eliminated through normalization, that is, the baseline drift noise due to movement is eliminated, as shown in FIG. 6.

2. Elimination of Step Noise by Differentiation

Figure 7:
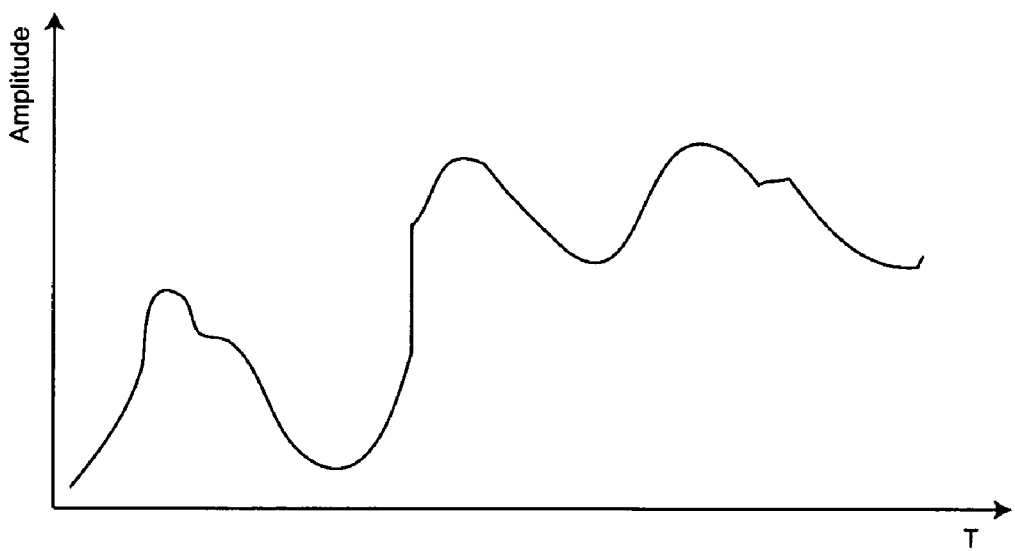
FIG. 7 shows a plethysmogram waveform including step noise.
Figure 8:
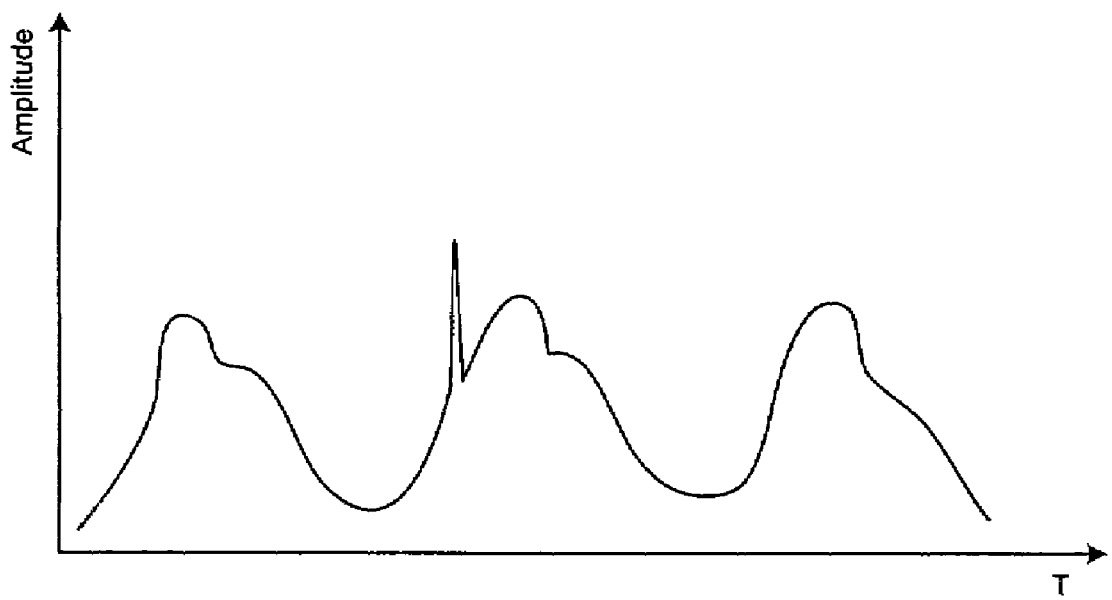
FIG. 8 shows a plethysmogram waveform including step noise after differentiation.

The step noise may be generated due to abrupt extrusion of the medium caused by vibration, as shown in FIG. 7. By differentiation, it becomes an impluse function similar to the δ function, as shown in FIG. 8. In this case, a three-point or five-point median filtering may be performed to eliminate the step noise.

3. Elimination of Impulsive Noise by Differentiation

Figure 9:
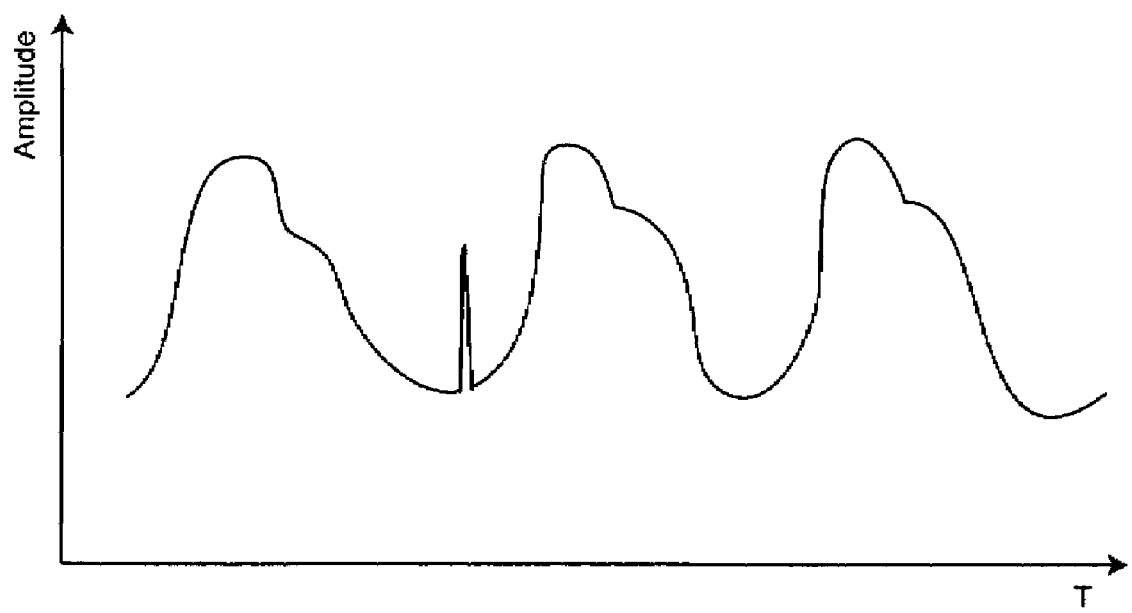
FIG. 9 shows a plethysmogram waveform including impulsive noise.
Figure 10:
FIG. 10 shows a plethysmogram waveform including impulsive noise after differentiation.

As to the mutation of the sampled value due to vibration, i.e., the impulsive noise similar to the δ function (as shown in FIG. 9), having been differentiated, it becomes the positive and negative double impulse functions, as shown in FIG. 10. In this case, a five-point median filtering may be performed to eliminate the impulsive noise.

As mentioned above, after processing the plethysmogram through differentiation and median filtering, the baseline drift, step noise and impulsive noise in the red light and infrared light plethysmogram signal may be eliminated.

4. Restoration of Waveform by Integration

Figure 11:
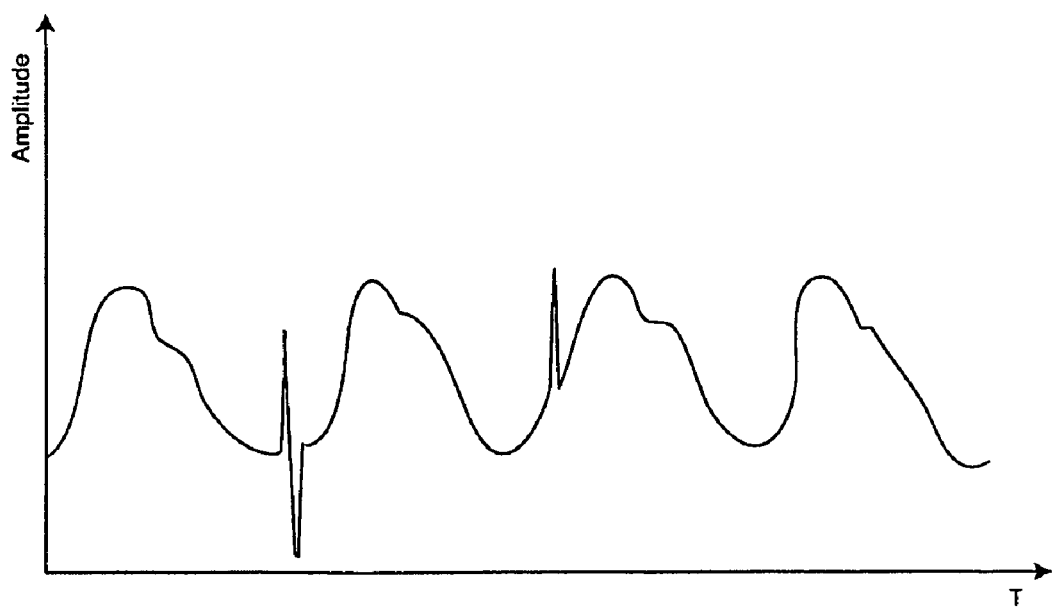
FIG. 11 shows a plethysmogram waveform resulting from differentiation of the waveform as shown in FIG. 4.

Having been processed by the above differentiation and median filtering, the plethysmogram including noise shown in FIG. 4 has a waveform as shown in FIG. 11. By further integrating the equations (16), (17):

from $\int_{t_0}^{t_1} \frac{dRed}{dt} = \int_{t_0}^{t_1} \frac{dRed_{sig}}{dt} \int_{t_0}^{t_1} \frac{dn_{Red}}{dt}$, it is derived that: (20)

$Red = Red_{sig} + n''_{Red};$ from $\int_{t_0}^{t_1} \frac{dIr}{dt} = \int_{t_0}^{t_1} \frac{dIr_{sig}}{dt} + \int_{t_0}^{t_1} \frac{dn_{Ir}}{dt}$, it is derived that: (21)

$Ir = Ir_{sig} + n''_{Ir};$ where $n_{Red}''$ and $n_{Ir}''$ are the remaining white noise portions of the plethysmogram noise after whitening processing.

This integration functions to restore the plethysmogram waveform, and at this point of time the waveform has become smoothed. The previously mentioned waveform differentiation corresponds to a whitening processing of the plethysmogram which eliminates the non-white noise from the noise.

5. Elimination of Nonlinear Slow Baseline Drift by Fitting

The principle of fitting is to obtain the low order approximation of arbitrary curves. Therefore, with the fitting approximation subtracted, higher order signal remains.

Usually the calculation of the pulse oxygen makes use of data within a few seconds, while the baseline drift in this short period generally has not many inflection points. A method of baseline fitting by the least-squares procedure is proposed herein, which has been proved in practice to well eliminate the baseline drift.

Assuming that the sampling frequency is $|f=1/T_s|[z1]$ and the sampling sequence is $T=[t_0 \ldots t_1 \ldots t_{n-1}]^t[z2]$, the sampling sequences of the red light and the infrared light are $Red=[red_0\ red_1 \ldots red_{n-1}]^t$, $Ir=[ir_0\ ir_1 \ldots ir_{n-1}]^t$. If baseline fitting is to be performed by the third order curve, and the coefficient matrix of the third order linear equations is $C=[c_0\ c_1\ c_2\ c_3]^t$, then $$\begin{bmatrix} 1 & t_0 & t_0^2 & t_0^3 \\ 1 & t_1 & t_1^2 & t_1^3 \\ \vdots & \vdots & \vdots & \vdots \\ 1 & t_{n-1} & t_{n-1}^2 & t_{n-1}^3 \end{bmatrix} \begin{bmatrix} c_0 \\ c_1 \\ c_2 \\ c_3 \end{bmatrix} = \begin{bmatrix} red_0 \\ red_1 \\ \vdots \\ red_{n-1} \end{bmatrix}, \quad (22)$$

that is, $[1\ T\ T^2\ T^3]C=Red$, whereby the coefficient matrix is:

$$C=[1TT^2T^3]^{-1}Red \quad (23)$$

Similarly, the coefficient matrix of the infrared light drift fitting curve may be obtained.

Figure 12:
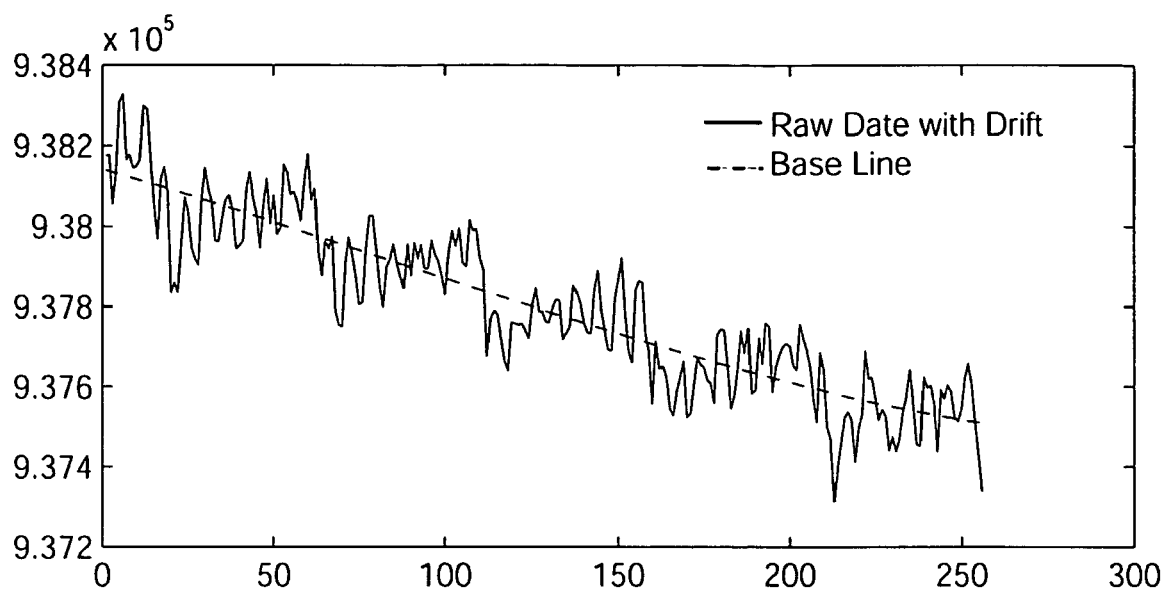
FIG. 12 shows a plethysmogram having baseline drift.
Figure 13:
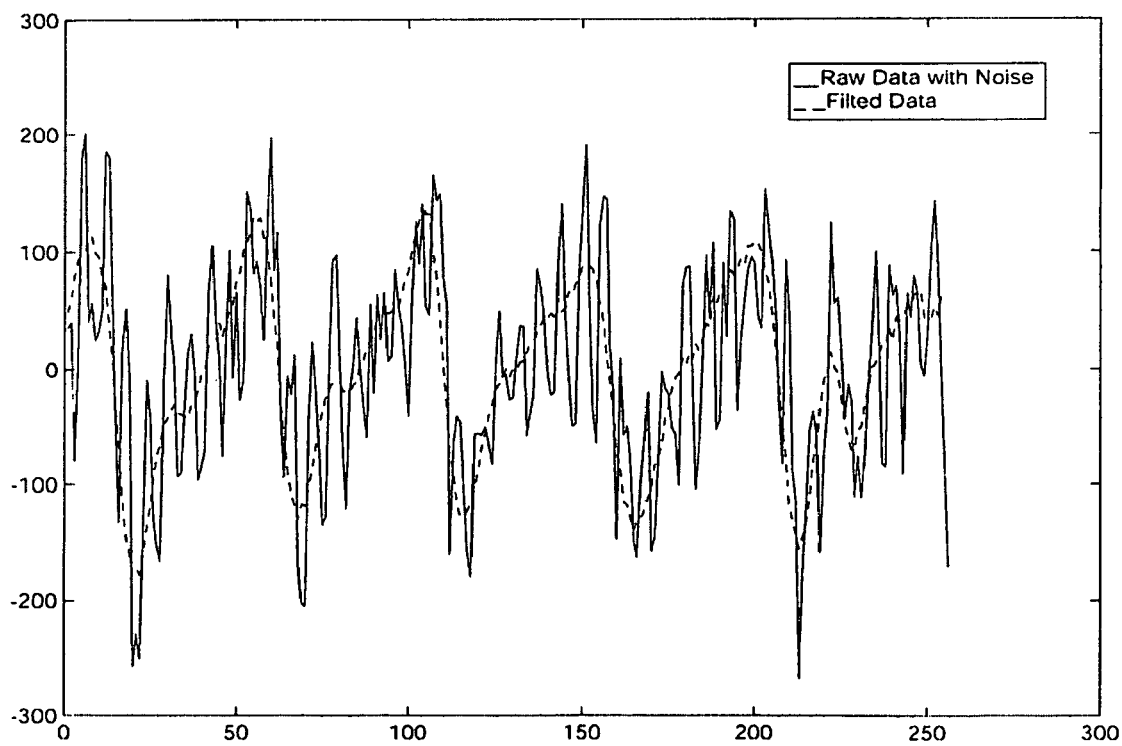
FIG. 13 shows a filtered plethysmogram, which is removed of the baseline drift through fitting.

When there is a drift in the weak perfusion data, the data free of baseline drift may be obtained by subtracting the fitting curve from the original sampled data curve with baseline drift. As shown in FIGS. 12 and 13, wherein the dotted line represents the baseline, the sampled data exhibits a very remarkable baseline drift before signal processing. By subtracting the baseline drift through fitting, the weak perfusion signal assumes the property of plethysmogram.

The fitting processing may also be performed by using the B spline function, which gives the similar result.

6. The Principle of Area Integration Recursive Algorithm

With equations (20) and (21) integrated respectively, the following ratio is obtained:

$$\frac{\int_{t_0}^{t_1} |a_0\cos(\omega t) + a_1\cos(2\omega t) + \ldots + a_{n-1}\cos(\omega t) + n''_{Red}|\ d(\omega t)}{\int_{t_0}^{t_1} |b_0\cos(\omega t) + b_1\cos(2\omega t) + \ldots + b_{n-1}\cos(n\omega t) + n''_{Ir}|d(\omega t)} = \quad (24)$$

$$\frac{4a_0\sin(\omega t)\Big|_0^{\pi/2} + \int_{t_0}^{t_1} |n''_{Red}|d(\omega t)}{4b_0\sin(\omega t)\Big|_0^{\pi/2} + \int_{t_0}^{t_1} |n''_{Ir}|d(\omega t)}$$

If the noise within a time interval may be regarded as the white noise, the integration value thereof is zero, thus the above equation becomes:

$$\frac{4a_0\sin(\omega t)\Big|_0^{\frac{\pi}{2}} + \int_{t_0}^{u_1} |n_{Red}^{\vee}| d(\omega t)}{4b_0\sin(\omega t)\Big|_0^{\frac{\pi}{2}} + \int_{t_0}^{u_1} |n_{Ir}^{\vee}| d(\omega t)} = \frac{a_0}{b_0} = \frac{Red_{AC}}{Ir_{AC}}. \quad (25)$$

Figure 14:
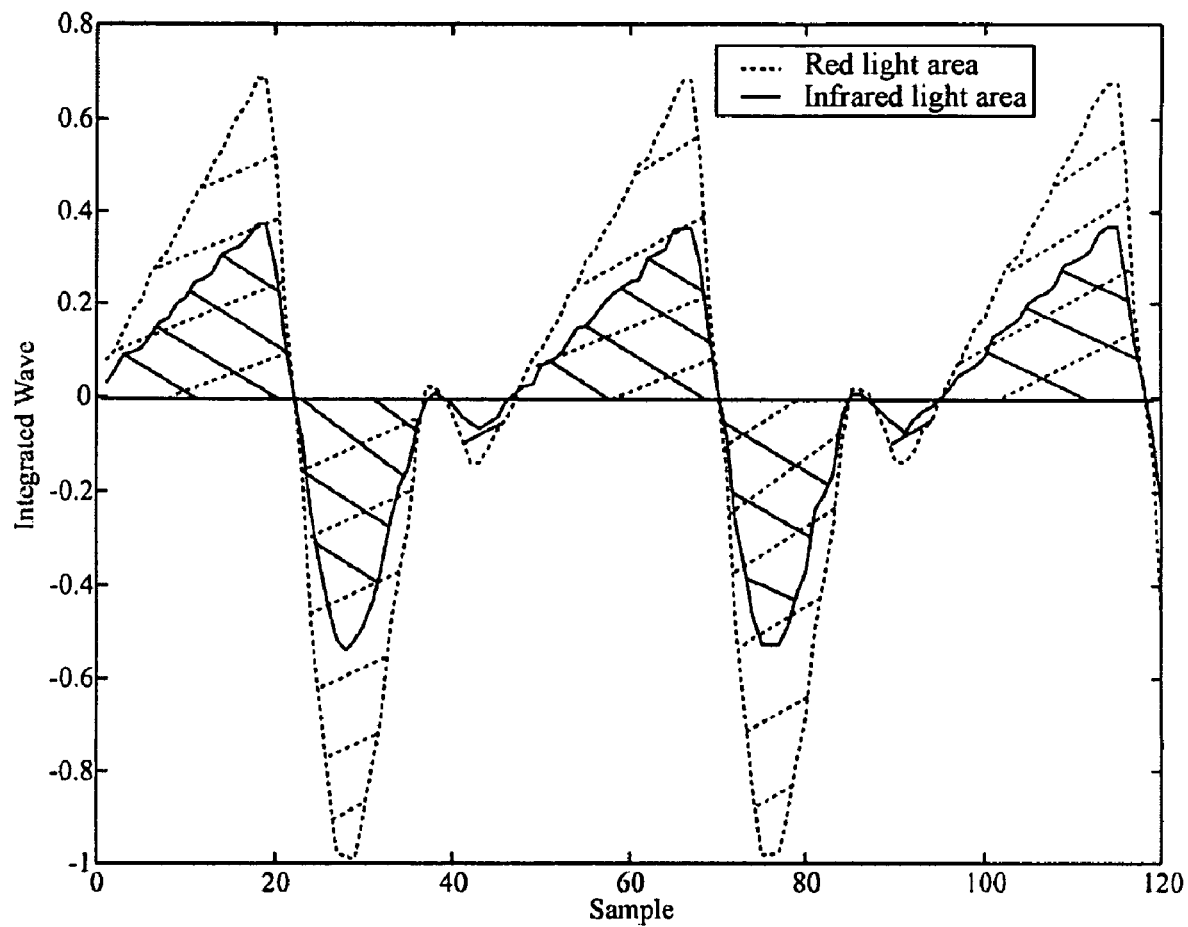
FIG. 14 shows the integration graph of a plethysmogram waveform.

According to the fact that the area ratio equals to the AC ratio, the ratio of the AC components of the two light beams may be calculated. Therefore, the integration value of the noise tends to be zero as long as the integration time interval is long enough. In this case, the integration data within a time interval may be used instead of the AC data of the two light beams obtained through location of the extreme values in the waveform. Moreover, since such a method eliminates the noise interference, good measurement can be obtained under the movement condition. FIG. 14 shows the integration graph of plethysmogram.

The above description is based on the assumption that the oxygen saturation of the object to be measured does not change within a time interval. In such a case, the longer the integration time interval, the better is the result of measurement, which is closer to the reality. However, when the oxygen saturation of the object to be measured varies, it is disadvantageous if the integration time interval is too long, which would reduce the measuring sensitivity. In the worst case, if integration starts at the beginning of the measurement, the phenomenon of data saturation would occur. After a time interval, the newly measured data would have little influence on the result, thus weakening the function of real time measurement.

To address the above problem, integration is performed only in a limited time interval. In the meanwhile, a forgetting factor $\lambda$ is introduced for maintaining the influence of the previous measurement and at the same time preventing it from getting too excessive. Then the ratio of AC components of the two light beams is obtained by the following formula:

$$\frac{Red_{AC}}{Ir_{AC}} = \frac{Red_{AC_0} + \lambda Red_{AC_1} + \ldots + \lambda^n Red_{AC_n}}{Ir_{AC_0} + \lambda Ir_{AC_1} + \ldots + \lambda^n Ir_{AC_n}}. \quad (26)$$

When $0<\lambda<1$, after iteration for a number of times, the preceding data gives no influence. Empirically, it is comparatively reasonable to take $\lambda$ as 0.8.

Figure 15:
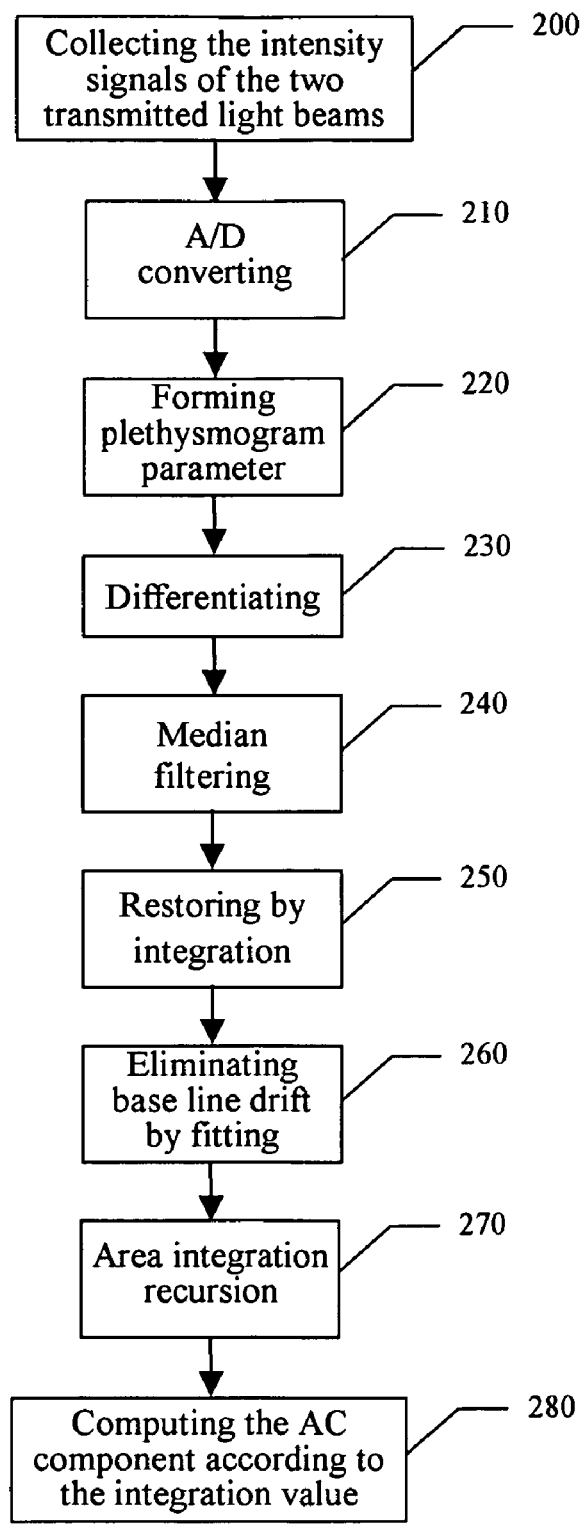
FIG. 15 shows a flow chart of one embodiment of the present invention.

According to the above principle, the measurement of AC component preferably comprises the following steps of, as shown in FIG. 15:

In step 200, collecting the respective optic signals of the first wavelength light (such as the red light) and the second wavelength light (such as the infrared light) transmitting through the biologic tissue terminals, and converting the optic signals into electric signals, then go to step 210;

In step 210, converting the analog electric signals into digital signals, then in step 220, generating respective plethysmogram data with the digital signals, and go to step 230;

In step 230, processing the plethysmogram data of the two light beams by differentiation respectively, then in step 240 processing the data obtained after differentiation by normalization and median filtering respectively, to eliminate non-white noise from the noise, wherein the median filtering is preferably a five-point median filtering, then go to step 250;

In step 250, performing the first time integration of the plethysmogram data of the two light beams obtained after normalization and median filtering respectively, the purpose of which is to restore the plethysmogram waveform, then go to step 260;

In step 260, performing the least-squares fitting procedure for the plethysmogram waveform of the two transmitted light beams to eliminate nonlinear baseline drift, respectively. This step specifically comprises the following steps of:

calculating the respective fitting curve coefficient matrixes of the drift baseline according to the sampling frequencies and sampling sequences of the transmitted light intensity of the first wavelength light and the second wavelength light;

subtracting the corresponding fitting curves from the plethysmogram waveform curves of the transmitted first wavelength light and second wavelength light.

after smoothing waveforms of the two light beams, calculating the oxygen saturation according to the waveform, preferably by area integration method, subsequently:

In step 270, performing the second time integration on the processed plethysmogram waveforms of the two light beams respectively, the integration being area integration, then go to step 280;

In step 280, calculating the oxygen saturation according to integration values of the two-wavelength light. In particular, two methods can be adopted, the first of which is to directly divide one integration value by the other, so as to obtain the ratio of AC components between the two light beams. According to the formula:

$$R = \frac{Red_{AC}/Red_{DC}}{Ir_{AC}/Ir_{DC}} = \frac{Red_{AC}}{Red_{DC}} \cdot \frac{Ir_{DC}}{Ir_{AC}} = \frac{Ir_{DC}}{Red_{DC}} \cdot \frac{Red_{AC}}{Ir_{AC}},$$

the value of R is calculated, then according to formula (10), the oxygen saturation is calculated.

The second method is to multiply the previous integration values of the two-wavelength light by a forgetting factor $\lambda$, then add the thus obtained value with the current integration value by iteration, and then calculate the ratio. The formula is as follows:

$$\frac{Red_{AC}}{Ir_{AC}} = \frac{Red_{AC_0} + \lambda Red_{AC_1} + \ldots + \lambda^n Red_{AC_n}}{Ir_{AC_0} + \lambda Ir_{AC_1} + \ldots + \lambda^n Ir_{AC_n}},$$

where $\lambda$ is the forgetting factor, and $0<\lambda<1$. Empirically, $\lambda=0.8$. The time interval for integration each time preferably ranges from 2 to 3 seconds.

The above step not only eliminates the non-white noise by differentiation, but also eliminates the white noise by area integration.

Among the above steps, step 260 may be unnecessary according to circumstances, or may be arranged to be executed before or after the differentiation step, preferably after the first time integration step.

The waveform method is also capable of calculating oxygen saturation, whereby oxygen saturation is calculated by locating the maximum value and minimum value of the waveform of the two light beams according to the waveform obtained after differentiation. This method is a prior art method, and thereby is not illustrated in details herein.

Figure 16:
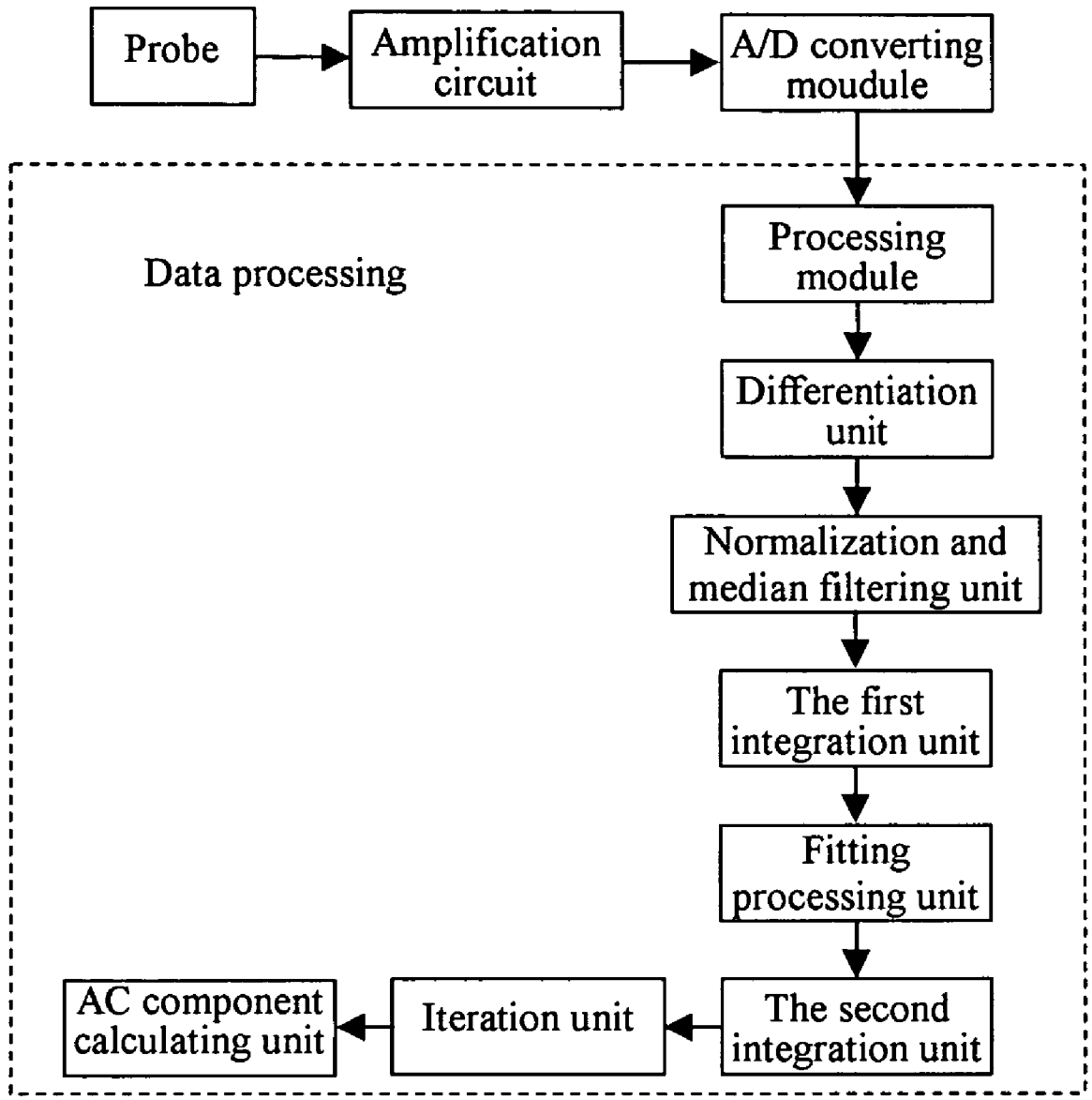
FIG. 16 shows a block diagram of the structure of one embodiment of the present invention.

A preferable apparatus for performing the above method has the structure as shown in FIG. 16, comprising: a collecting module (i.e., probe), an amplification circuit, an A/D converting module, a processing module, a noise eliminating module (including a differentiation unit and a normalization and median filtering unit), a restoring module (i.e., the first integration unit), a fitting unit, a second integration unit, an iterating unit and an AC component calculating unit which are connected in series.

The probe comprises a luminotron for emitting the first wavelength light (e.g., the red light) and the second wavelength light (e.g., the infrared light), and a phototube. The phototube corresponding with the luminotron is useful for receiving the corresponding light after the first wavelength light and the second wavelength light transmit through the biologic tissue terminals, and for converting the received optic signals into corresponding electric signals; the amplification circuit is useful for amplifying the electric signals; the A/D converting module is useful for converting the electric signals into digital signals; the differentiation unit is useful for differentiating the plethysmogram of the first wavelength light and the second wavelength light; the normalization and median filtering unit is useful for normalizing and median filtering the plethysmogram of the first wavelength light and the second wavelength light obtained after differentiation, respectively, and outputting the same to the first integration unit; the first integration unit is useful for integrating the plethysmogram of the first wavelength light and the second wavelength light obtained after differentiation; the fitting unit is useful for performing the least-squares fitting procedure upon the plethysmogram waveform of the transmitted first wavelength light and second wavelength light, respectively, to eliminate nonlinear slow baseline drift; the second integration unit is useful for area integrating the plethysmogram of the first wavelength light and the second wavelength light obtained after the first integration; the iterating unit is useful for receiving the output of the second integration unit, and performing the iteration processing after multiplying the integration values of the first wavelength light and the second wavelength light obtained after the second integration by a forgetting factor, respectively, and outputting the result to the AC component calculating unit, wherein the forgetting factor is greater than 0 but less than 1; the AC component calculating unit is useful for dividing the integration value of the first wavelength light obtained after the second integration by that of the second wavelength light, and using the result as the ratio of the AC components of the two light beams.

In the above embodiment, the differentiation unit, the normalization and median filtering unit, the first integration unit, the fitting processing unit and the AC component calculating unit may be designed within a single chip processor, and may also be integrated in other semiconductor chips.

Figure 17:
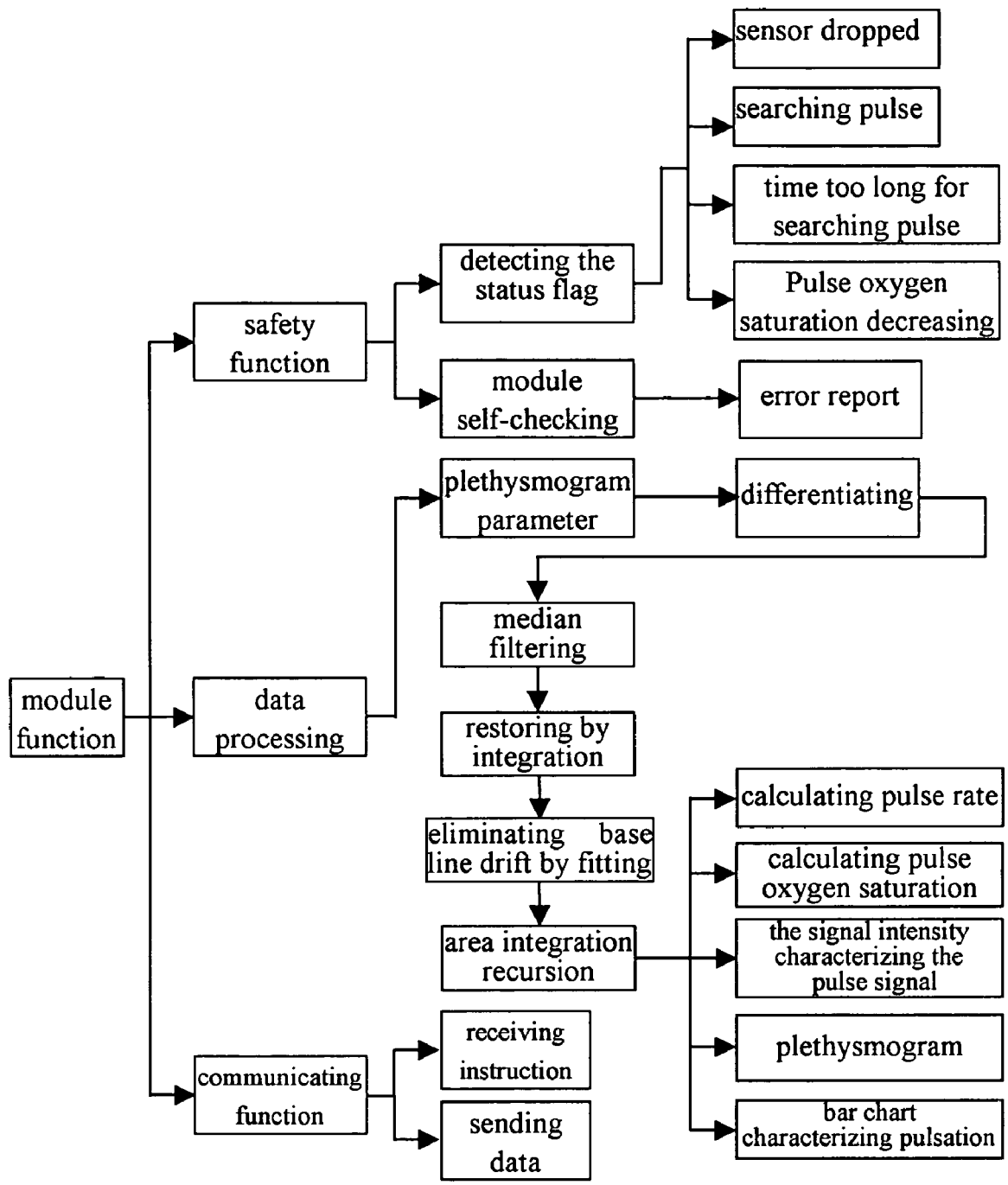
FIG. 17 shows a system flow chart of one embodiment of the present invention.

The system flow chart according to the present invention is shown in FIG. 17:

1. After the system is powered on, hardware initialization, and subsequent CPU system self-checking and program initialization start;

2. The collecting module collects data in real time, which data is then stored in the data buffer to serve as a basis for data processing and the calculation of oxygen saturation and pulse rate parameters;

3. Given the collected data, the control module performs different control over the hardware in each state, and the control over the A/D sampling (including the internal A/D and external A/D), as well as the control over the drive current of the luminotron and the bias circuit and gain;

4. Having processed the collected data to obtain the plethysmogram parameters, the data processing module is capable of calculating the pulse rate and oxygen saturation after eliminating the plurality of noises by differentiation, median filtering, integration restoration, elimination of baseline drift by fitting, and area integration recursion, and is also capable of obtaining the signal intensity characterizing the pulse signal. In addition, the plethysmogram and bar chart characterizing pulsation can be plotted.

5. Meanwhile, the system has the safety alarm function and self-checking function upon power-on. The system can monitor the decreasing of the oxygen saturation during normal measurement, and alarm in case the sensor is dropped, the pulse is being searched, the pulse searching time is too long, and the like.

Figure 18:
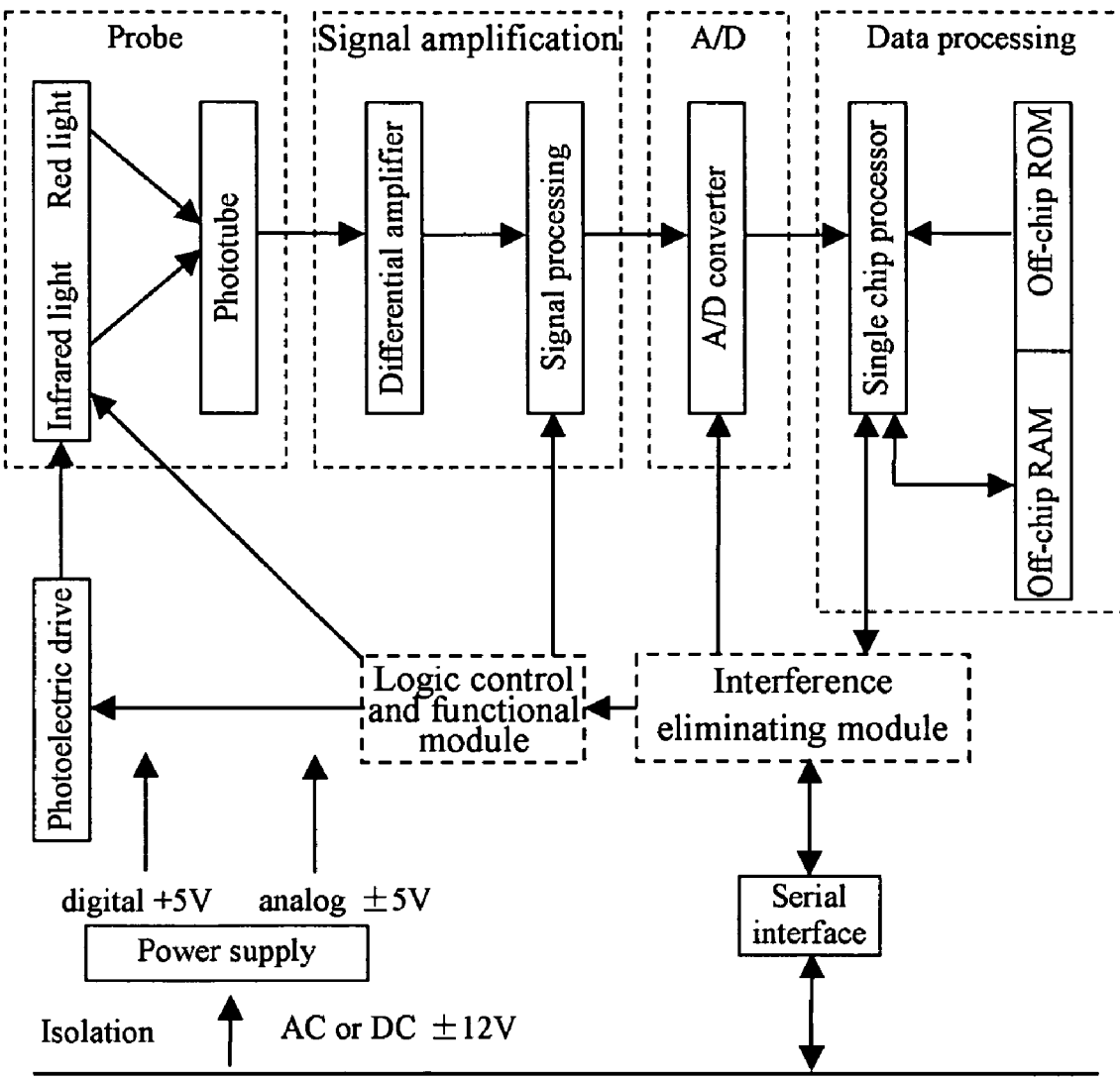
FIG. 18 shows a block diagram of the structure of another embodiment of the present invention.

Another embodiment of apparatus for eliminating interference in pulse oxygen measurement according to the present invention is shown in FIG. 18, comprising: a probe unit, a signal amplification unit, an A/D converting module, a single chip data processing unit, a logic control module and a power supply circuit which are connected in series. The apparatus differs from the prior art in that the single chip data processing unit comprises a module capable of eliminating interference, and the output terminals of this interference eliminating module are connected with the A/D converting module and logic control and functional module respectively. The probe unit comprises a red light source, an infrared light source and the light driver circuit and phototube thereof. The signal amplification unit comprises a differential amplification circuit and signal processing circuit. The flow chart for realizing the system is as follows:

After the system is powered on, hardware initialization, and subsequent CPU system self-checking and program initialization start;

The probe unit collects data in real time, which data is then stored in the data buffer to serve as the basis for data processing and the calculation of oxygen saturation and pulse rate parameters;

Given the collected data, the logic control module performs different control over the hardware in each state, and the control over the AD sampling (including the internal AD and external AD), as well as the control over the drive current of the luminotron and the bias circuit and gain;

The interference eliminating module is the core module, which is used to eliminate the non-white noise by differentiation of the plethysmogram, and at the same time calculate the pulse rate, and then calculate the oxygen saturation by the integration recursion algorithm.

The present invention is described by particular examples as mentioned above, which shall by no means be construed as a limitation to the present invention, but an illustration thereof instead. Those skilled in the art may understand that, according to the teachings of the present invention, a plurality of combinations may be realized by using the steps and various modules of the present invention. In addition, the method of the present invention can be realized not only by physical modules, but also by software modules. Therefore, various modifications, changes, variations, and other equivalent substitutions may be made without departing from the spirit and scope of the present invention. The present invention is intended to cover alternatives, modifications, and equivalents that may fall within the spirit and scope of the present invention as defined by the claims.

What is claimed is:

1. A method for eliminating interference in oxygen content measurement, comprising:

collecting a first wavelength light and a second wavelength light transmitting through an object to be measured, and converting collected signals into electric signals to form a plethysmogram;

normalizing the plethysmogram and decomposing the normalized plethysmogram into a combination of an ideal plethysmogram and a noise component and to expand the ideal plethysmogram by using functions that make up an orthonormal system;

eliminating the noise component in the plethysmogram by performing at least one differentiation operation upon the plethysmogram, in which the noise component comprises a first noise component caused by motion or movement of the object during the oxygen content measurement, and a constant corresponding to the first noise component is generated by performing the at least one differentiation operation;

and restoring the plethysmogram without the noise component through an integration operation.

2. The method of claim 1, further comprising:
conducting an analog-to-digital conversion to the electric signals to form a digitalized plethysmogram for subsequent processing.

3. The method of claim 1, further comprising:
performing curve fitting to eliminate a nonlinear slow baseline drift and subsequently calculating oxygen saturation, the action of fitting further comprising:
computing one or more respective drift baseline fitting curve coefficient matrices according to at least one or more sampling frequencies and one or more sampling sequences of a transmitted light intensity of the first wavelength light and the second wavelength light; and
subtracting one or more corresponding fitting curves from plethysmogram waveform curves of the first wavelength light and second wavelength light.

4. The method of claim 1, wherein the action of normalizing the plethysmogram comprises expanding the ideal plethysmogram by using one or more trigonometric functions that make up an orthonormal system.

5. The method of claim 1, wherein the action of eliminating the noise component comprises:
differentiating the plethysmogram having been processed, and
normalizing the plethysmogram that has been differentiated to eliminate a baseline drift noise caused by movement.

6. The method of claim 1, wherein the action of eliminating the noise component comprises:
differentiating the plethysmogram having been processed to transform the noise component caused by abrupt extrusion of an object to be measured into an impulse-function in a form of a δ function; and
conducting a three-point or five-point median filtering to eliminate the noise component.

7. The method of claim 1, wherein the action of eliminating the noise component comprises:
differentiating the plethysmogram having been processed to transform the noise component caused by mutation of a sampled value into positive and negative double impulse functions, and
conducting a five-point median filtering to eliminate the noise component.

8. The method of claim 3, wherein the oxygen saturation calculation is carried out by an area integration recursive algorithm, comprising:
integrating the plethysmogram having been restored in a period of time to eliminate a white noise occurring in the period of time and to obtain a ratio between a first AC component of the first wavelength light and a second AC component of the second wavelength light;

introducing a factor $\lambda$ to determine the ratio according to a formula listed below after a number of iterations:

$$\frac{Red_{AC}}{Ir_{AC}} = \frac{Red_{AC_0} + \lambda Red_{AC_1} + \ldots + \lambda^n Red_{AC_n}}{Ir_{AC_0} + \lambda Ir_{AC_1} + \ldots + \lambda^n Ir_{AC_n}}$$

9. The method of claim 8, wherein the period of time ranges from 2 to 3 seconds, and the factor comprises a value being in a range of $0 < \lambda < 1$.

10. The method of claim 9, wherein the value is 0.8.

11. The method of claim 1, wherein the first wavelength light and the second wavelength light comprises a red light and an infrared light respectively.

12. An apparatus for eliminating interference in pulse oxygen measurement, comprising:
a collecting module including a luminotron and a corresponding phototube that is adapted to collect a first wavelength light and a second wavelength light transmitting through an object to be measured and is adapted to convert collected signals into electric signals to form a plethysmogram;
a processing module that is adapted to normalize the plethysmogram and decompose the plethysmogram into a combination of an ideal plethysmogram and a noise component and is adapted to expand the ideal plethysmogram by using at least functions that make up an orthonormal system;
a noise eliminating module that is adapted to eliminate the noise component in the plethysmogram through at least a differentiation operation including a differential operator, in which
the noise component comprises a first noise component caused by motion or movement of the object during the oxygen content measurement, and a constant corresponding to the first noise component is generated by performing the at least one differentiation operation;
and a restoring module that is adapted to restore the plethysmogram without the noise component through an integral operation.

13. The apparatus of claim 12, further comprising:
a converting module that is adapted to perform analog-to-digital conversion of the electric signals to form a digitalized plethysmogram.

14. The apparatus of claim 12, further comprising:
a fitting module that is adapted to compute respective drift baseline fitting curve coefficient matrices according to at least one or more sampling frequencies and one or more sampling sequences of an intensity of the first wavelength light and an intensity of the second wavelength light and is adapted to subtract corresponding fitting curves from plethysmogram waveform curves of the first wavelength light and the second wavelength light to eliminate a nonlinear baseline drift.

15. The apparatus of claim 14, wherein at least one of the fitting module, the processing module, the noise eliminating module, and the restoring module comprises either a physical module or a computer-executable software module.

16. The apparatus of claim 12, wherein the functions that make up the orthonormal system comprise trigonometric functions.

17. The apparatus of claim 12, wherein the noise eliminating module is adapted to execute the following functions:
differentiating the plethysmogram having been processed by using the processing module, and normalizing the plethysmogram that has been differentiated to eliminate a baseline drift noise caused by movement.

18. The apparatus of claim 12, wherein the noise eliminating module is adapted to execute the following functions:

differentiating the plethysmogram having been processed by the processing module to transform the noise component caused by abrupt extrusion of the object to be measured into an impulse function in a form of a δ function; and conducting a three-point or five-point median filtering to eliminate the noise component.

19. The apparatus of claim 12, wherein the noise eliminating module is adapted to execute the following functions:

differentiating the plethysmogram having been processed by the processing module to transform the noise component caused by mutation of a sampled value into positive and negative double impulse functions; and conducting a five-point median filtering to eliminate the noise component.

20. The apparatus of claim 12, wherein the first wavelength light and the second wavelength light comprise a red light and an infrared light respectively.

* * * * *